US007211551B2

(12) United States Patent
McDonald

(10) Patent No.: US 7,211,551 B2
(45) **Date of Patent: *May 1, 2007**

(54) UNIVERSAL CLEANER THAT CLEANS TOUGH OIL, GREASE AND RUBBER GRIME AND THAT IS COMPATIBLE WITH MANY SURFACES INCLUDING PLASTICS

(76) Inventor: Mary E. McDonald, 6216 Belmore La., Hopkins, MN (US) 55343

( * ) Notice: Subject to any disclaimer, the term of this patent is extended or adjusted under 35 U.S.C. 154(b) by 151 days.

This patent is subject to a terminal disclaimer.

(21) Appl. No.: 10/690,208

(22) Filed: Oct. 21, 2003

(65) Prior Publication Data

US 2004/0121927 A1 Jun. 24, 2004

Related U.S. Application Data

(60) Provisional application No. 60/420,050, filed on Oct. 21, 2002.

(51) Int. Cl.
*A61K 8/00* (2006.01)

(52) U.S. Cl. ...................... 510/130; 510/432; 510/505; 510/506; 134/42

(58) Field of Classification Search ..................... None
See application file for complete search history.

(56) References Cited

U.S. PATENT DOCUMENTS

| | | | | |
|---|---|---|---|---|
| 3,998,743 | A | 12/1976 | Maly et al. | 252/8.55 B |
| 4,282,132 | A | 8/1981 | Benda et al. | 260/30.2 |
| 4,435,305 | A | 3/1984 | Tsoukalas et al. | 252/158 |
| 4,608,086 | A | 8/1986 | Dodge | 106/12 |
| 4,676,920 | A | 6/1987 | Culshaw | 252/163 |
| 4,780,228 | A | 10/1988 | Gardiner et al. | 252/51 |
| 4,792,413 | A | 12/1988 | Nash et al. | 252/111 |
| 4,820,776 | A | 4/1989 | Kapuscinski et al. | 525/279 |
| 4,859,359 | A | 8/1989 | DeMatteo et al. | 252/174.15 |
| 4,952,637 | A | 8/1990 | Kapuscinski et al. | 525/279 |
| 5,122,194 | A | 6/1992 | Miller et al. | 134/29 |
| 5,145,523 | A | 9/1992 | Halpin et al. | 106/287.24 |
| 5,188,754 | A | 2/1993 | Weltman et al. | 252/162 |
| 5,207,838 | A * | 5/1993 | Googin et al. | 134/42 |
| 5,254,290 | A | 10/1993 | Blandiaux et al. | 252/545 |
| 5,290,472 | A | 3/1994 | Michael | 252/170 |
| 5,342,549 | A | 8/1994 | Michael | 252/546 |
| 5,421,906 | A | 6/1995 | Borah | 134/26 |
| 5,454,969 | A | 10/1995 | Fields et al. | 252/162 |
| 5,512,202 | A | 4/1996 | Borah | 252/142 |
| 5,531,933 | A | 7/1996 | Masters et al. | 510/429 |
| 5,667,594 | A | 9/1997 | Omure et al. | 134/26 |
| 5,690,539 | A | 11/1997 | Swidler et al. | 451/38 |
| 5,710,108 | A | 1/1998 | McNally et al. | 507/110 |
| 5,728,660 | A | 3/1998 | Borah | 510/110 |
| 5,763,734 | A * | 6/1998 | Nachtman et al. | 588/1 |
| 5,773,398 | A | 6/1998 | Joye et al. | 510/245 |
| 5,811,383 | A * | 9/1998 | Klier et al. | 510/417 |
| 5,821,211 | A | 10/1998 | Borah | 510/247 |
| 5,961,736 | A | 10/1999 | Borah et al. | 134/26 |
| 5,977,042 | A | 11/1999 | Hernandez et al. | 510/201 |
| 6,011,192 | A | 1/2000 | Baker et al. | 585/818 |
| 6,200,352 | B1 | 3/2001 | Romack et al. | 8/142 |
| 6,401,731 | B2 | 6/2002 | Robertson | 134/22.19 |
| 6,497,769 | B1 * | 12/2002 | Martin | 134/10 |
| 6,583,097 | B2 * | 6/2003 | McDonald | 510/365 |
| 6,605,158 | B1 * | 8/2003 | Martin | 134/10 |
| 6,652,661 | B2 * | 11/2003 | Martin | 134/10 |

OTHER PUBLICATIONS

Mary McDonald, "Prior Art Cleaners," pp. 1-14.

* cited by examiner

*Primary Examiner*—Gregory Webb
(74) *Attorney, Agent, or Firm*—Kagan Binder, PLLC

(57) ABSTRACT

Versatile cleaning composition that has tremendous cleaning power, yet is compatible with many surfaces. For example, the cleaning composition easily cleans oil, grease, tar, and rubber from soiled surfaces, but does not damage metals, vehicle paints, concrete, plastics such as polycarbonate, MYLAR polyester and silicone sealants, wood, ceramic, and the like. The cleaning composition includes an oil solubilizing amount of a degreaser, a rubber solubilizing amount of a rubber solvent, and a polar, organic diluent. In preferred embodiments, the degreaser comprises a glycol ether, the rubber solvent comprises an nonaromatic naphtha, and the diluent comprises an alcohol.

24 Claims, No Drawings

UNIVERSAL CLEANER THAT CLEANS TOUGH OIL, GREASE AND RUBBER GRIME AND THAT IS COMPATIBLE WITH MANY SURFACES INCLUDING PLASTICS

CROSS-REFERENCE TO RELATED APPLICATIONS

This non-provisional patent application claims the benefit of priority from U.S. provisional application No. 60/420,050 filed Oct. 21, 2002, incorporated herein by reference in its entirety.

FIELD OF THE INVENTION

This invention is in the field of cleaning compositions. More specifically, this invention relates to cleaning compositions including a rubber solvent, a degreaser, and a diluent. The compositions can be used to clean oil, grease, tar, rubber, organic matter, particulate matter, and other debris from soiled surfaces. The compositions also are particularly advantageously used in cleaning methodologies for the removal of contaminants such as radionuclides, PCB's, herbicides, pesticides, and heavy metals from contaminated materials. The compositions may also be used as an effective cleaner to remove grease, paint, stain, glue, and other grime from the hands or other body surfaces.

BACKGROUND OF THE INVENTION

Some environments generate a tough combination of dirt, grime, soil, and debris that is very difficult to clean effectively with only one cleaner. One example of such an extreme environment is the vehicle race track, e.g., auto speedway, truck speedway, or the like. In the course of a race, windshields are splattered both with oils (e.g., motor oils and gear oils) and with rubber bits thrown from race tires that erode during racing. Dirty windshields obscure the driver's visibility, impairing the safety of all race participants. Accordingly, it is common practice to try and clean race vehicle windshields during pit stops.

Cleaning a race vehicle windshield at a pit stop is not a simple matter, because this use imposes many stringent demands on a cleaner. In addition to being able to remove oils and rubber and other soil on the windshield, the cleaning agent must act to remove this grime very fast, i.e., within the time constraints of the pit stop. The cleaner also must be easy to remove quickly from the surface. Desirably, therefore, the cleaner must not only act fast, but also evaporate at a quick enough rate so that the time spent wiping the windshield with a clean cloth, squeegee, or the like, will be at a minimum. While quick cleaning action is important, this must also be balanced against residence time. The cleaner components must evaporate at a slow enough rate so that the cleaner has a long enough contact time with the soiled surface to remove the soils. Ideally, the cleaner also should go on and come off without requiring any rinsing with water or any other rinse agent.

Besides being fast and simple to use, the cleaner must be compatible with the race vehicle itself. Importantly, the cleaner must leave no residue behind that might obscure visibility through the windshield. The cleaner also must not damage the LEXAN polycarbonate material that forms the windshield or the silicone sealant around the edge of the windshield. The cleaner must also be compatible with MYLAR polyester, because a clear plastic sheet, often made of MYLAR polyester and called a "tear-away", often is used to cover the windshield. The "tear-away" is used to dampen impacts from particulate matter during the race and can be removed quickly during a pit stop when the sheet becomes so damaged that it obscures the race vehicle driver's view. Cleaners splashed across a windshield inevitably will contact the race vehicle body, too. Therefore, the cleaner must not damage the race vehicle's body paint. The cleaner also should provide good cleaning performance over a wide temperature range. For example, it would be very desirable to have a cleaner that provides good cleaning performance at temperatures ranging from 25° F. (−4° C.) to 140° F. (60° C.).

Race vehicle bodies and the walls at racetracks need to be cleaned, too. These surfaces also are splattered with the same soils as the windshield, including oils and rubber. Also, race vehicle bodies and/or racetrack walls may be smeared with rubber from the tires of other race vehicles that sideswipe such surfaces during races. For these surfaces, in addition to being able to remove oils and rubber under the stringent conditions described above, the cleaning agent must not unduly damage the inks or the backings of the promotional decals or other graphics that are affixed to the vehicle's body or the racetrack walls.

The racetrack, of course, is just one example of an environment in which oils and rubber collectively challenge a cleaner. There are many others, too. For example, automobiles, trucks, motorcycles, and the like also get splattered with oils, tar, rubber, bugs, and the like during the course of ordinary street driving. Industrial equipment, industrial floors which have been traversed and marked by tires, engines, motors, railways, railway cars, and the like may also suffer from such grime.

With the growth of industry, a significant amount of hazardous waste products and products formerly regarded as useful but now recognized as hazardous have entered the environment. These hazardous materials are frequently present as contaminants on surfaces of equipment, installations of all kinds, civil works, soil, and the like.

For example, a significant amount of radioactive waste, in the form of radionuclides, is present in nuclear power plants, nuclear weapons production plants, mining and milling equipment used for uranium mining, and in apparatus in the medical area where radioactive isotopes are used. The presence of these radionuclides, which contaminate equipment including pumps, pipelines, valves, concrete foundations, and all other equipment and structures with which the radionuclides have come into contact, now pose a serious health problem since their radioactivity is known to be carcinogenic. To qualify as a decontaminated facility, depending upon the type of radioactivity, the NRC requires that the level of radioactivity from radionuclides be reduced to less than 5,000 disintegrations per minute (DPM) in some cases and other lower levels in other cases.

Polychlorinated biphenyls (PCBs) were once widely used industrial chemicals, especially as insulating or hydraulic fluids in electrical capacitors, transformers, vacuum pumps, gas-transmission turbines, machinery, and various other devices and products. Their chemical stability and nonflammability contributed to their commercial usefulness. However, it has since been found that PCBs are carcinogens and the United States Environmental Protection Agency (EPA) currently lists PCBs and any surfaces or equipment containing PCBs as hazardous. Consequently, these chemicals are no longer recommended or used in new applications. However, a large amount of existing capital equipment, installed before the listing of PCBs as hazardous, contains PCBs. These installations pose a hazard whenever a spillage of PCBs occurs thereby contaminating the surrounding area or whenever routine repairs expose workers or the environment to PCBs.

While it is desirable to remove PCBs and dispose of these in a suitable hazardous waste facility, PCBs are not easily removed from apparatus or spilled areas because of their capability to enter into the tiniest of pores and microscopic voids and spaces in surfaces with which they come into contact. For example, in transformers which frequently contain wood, paper, metal joints, and electrical components with minute crevices, the PCBs soak into pores and microscopic voids in the steel and concrete and fill the tiniest of microscopic spaces such as pores and microscopic voids, and the like, in metals. When PCBs have spilled onto a surface, such as a concrete surface, the PCBs over time will soak into pores and microscopic voids in the concrete and contaminate the concrete to well below the exposed surface and into the underlying substrate. Current techniques that merely clean the surface of concrete that has been exposed to the PCBs for a long period of time are not able to adequately clean the surface and do not reach PCBs held in the substrate below the surface in the pores and microscopic voids. Moreover, once surface cleaning has been completed, PCBs leach from the pores and microscopic voids to the surface over time due to the effect of a concentration gradient. Thus, the surface becomes recontaminated and further cleaning is necessitated. Likewise, while the bulk of the PCBs can be readily drained from some PCB-containing equipment, the residual PCB contaminant in pores, microscopic voids, crevices, and joints is not easily removed. It is found that upon refilling the drained apparatus with a replacement fluid for PCBs, PCBs will continue to leach from surfaces of the apparatus into the replacement fluid thereby contaminating it and rendering it hazardous.

Likewise, heavy metals have been identified as hazardous to human health and the EPA requires their removal from environments where they pose a health hazard. Like PCBs and radionuclides, heavy metals have the capability to migrate into pores, joints, crevices, and microscopic voids in interior and exterior surfaces and thereby cause contamination in the substrate to well below the apparent surface of any apparatus, device, or ground surface with which they come into contact. Mere surface cleaning is therefore ineffective to remove heavy metals contamination from substrates.

Certain pesticides and herbicides are also now known to be hazardous to human health. These compositions contaminate surfaces and substrates, such as concrete, but more especially particulate surfaces, such as soil, clay, gravel, and the like.

There is a need for methods and cleaning compositions for the removal of contaminants including radionuclides, PCBs, herbicides, pesticides, and heavy metals from porous and non-porous interior and exterior surfaces, particulate surfaces, and surfaces having minute spaces, crevices, pores, or microscopic voids into which these contaminants migrate and from which they are not readily extractable. Further, the method and cleaning compositions should desirably not only extract these contaminants from well below the surface to be cleaned, but should extract these to such a level that any remaining contaminants do not pose a hazard, i.e., a surface and its underlying substrate cleaned of PCBs would meet EPA regulations for reclassification from a hazardous to a non-hazardous material; a surface and its substrate cleaned of heavy metals, herbicides, or pesticides, would meet the EPA's TCLP standard setting the upper limit for their concentration; and a surface and its substrate cleaned of radionuclides would test at less than 5,000 DPM. The method and cleaning compositions should also desirably extract these contaminants without significant surface damage or scarring. Further, the method and cleaning compositions should desirably extract these contaminants with a minimum amount of hazardous waste byproduct which must be disposed of and, in the case of radionuclides, the byproduct waste should preferably be water soluble to assist in ease of disposal. Finally, cleaning compositions should desirably not be flammable.

What is needed is a cleaner that has the power to clean oil, tar, rubber, bug residue, and other soils over a wide temperature range, yet will not damage metal, many paints, many inks, ceramic, wood, concrete, many plastics and/or the like.

SUMMARY OF THE INVENTION

The present invention provides an extremely versatile cleaning composition that has tremendous cleaning power, yet is compatible with many surfaces. For example, the cleaning composition easily cleans oil, grease, tar, and rubber from soiled surfaces, but does not damage metals, vehicle paints, concrete, plastics (such as polycarbonate, polyester and silicone sealants), wood, ceramic, and the like. The ability of the cleaner to clean such tough soils while still being gentle enough not to harm a wide range of surfaces is very surprising, since many conventional cleaners having comparable cleaning power will damage plastics and other surfaces. Preferred embodiments of the cleaner also works fast and leave no residue. It can be applied and wiped off, or otherwise removed, without delay after being applied. It will also clean effectively over a wide temperature range, including temperatures ranging from 25° F. (−4° C.) to 140° F. (60° C.) or more.

Accordingly, it can be appreciated that more volatile embodiments of the cleaner, i.e., those that dry relatively quickly, are particularly suitable for use in the racetrack environment. For example, it can be used to clean windshields very quickly during a pit stop. When a vehicle pulls in for a pit stop, a pit crew member can splash, pour, spray, or otherwise cause the cleaner to contact the windshield. Soil on the windshield will be quickly dissolved or otherwise loosened from the window surface. Without delay, the crew member can then use a cloth, sponge, squeegee or the like to immediately remove the cleaner and the loosened soil. In only a few seconds, the windshield is clean and ready for more racing action. Of course, the vehicle body may also be cleaned just as quickly, if desired. After the race, the other surfaces of the racetrack facility, e.g., walls, bleachers, pavement, and the like, may also be easily cleaned.

Race vehicle teams also have practice sessions and/or testing sessions before races and at other times. The vehicles get dirty in these sessions, too. The cleaner can also be used to clean the vehicles after these sessions, as well as after a race.

Other embodiments of the invention, i.e., those that are relatively less volatile, may be used in decontamination methodologies to help remove hazardous substances from contaminated materials. Thus, such embodiments of the invention provide cleaning compositions and methods for applying these compositions for the extraction of contaminants such as radionuclides, herbicides, pesticides, polychlorinated biphenyls (PCBs), heavy metals, and other hazardous compositions including those listed as hazardous under the U.S. EPA's TCLP standard, or mixtures thereof, from surfaces and their underlying substrates, of all kinds.

Embodiments of the invention are also provide a fast, effective way to remove grease, dirt, oil, soot, paint, stain, and other grime from the hands and other body surfaces.

DETAILED DESCRIPTION OF THE PRESENTLY PREFERRED EMBODIMENTS

The embodiments of the present invention described below are not intended to be exhaustive or to limit the invention to the precise forms disclosed in the following detailed description. Rather the embodiments are chosen and described so that others skilled in the art may appreciate and understand the principles and practices of the present invention.

Cleaning compositions of the present invention generally include one or more degreasers, one or more rubber solvents, and one or more polar, organic diluents. In the practice of the present invention, a degreaser is a fluid, slurry, or the like that is capable of solubilizing grease, oil, hydrocarbons, and the like. Preferred degreasers of the present invention satisfy the Oil Solubility Test. According to this test, two or three drops of 20W–50 racing motor oil are dropped into 2 ounces (59 ml) of the degreaser at room temperature. The degreaser is deemed to solubilize the oil and satisfy the test if the oil dissolves in the degreaser, optionally with stirring, to form a single phase mixture within no more than 10 to 20 seconds, preferably no more than 5 to 10 seconds.

Representative examples of suitable degreasers include a wide variety of organic solvents and generally include materials such as ketones, amines, esters, tetrahydrofuran or other heterocycles, alcohols, ethers, glycol ethers, combinations of these, and the like. Of these, one or more glycol ethers are particularly preferred for a variety of reasons. Firstly, glycol ethers have excellent oil dissolving capabilities. These compounds solubilize oil very quickly. It is believed that glycol ethers are such excellent solvents because they combine the solvent characteristics of both alcohols and ethers. Additionally, glycol ethers tend to form compatible, single phase mixtures with the other components of the cleaning composition, significantly without unduly compromising the cleaning power of those other ingredients. The volatility of glycol ethers is also in a suitable regime so that cleaning compositions incorporating these materials dry at a rate that is not too fast or too slow. Glycols ethers also are compatible with the race vehicle environment. When included as a constituent of the present invention, these compounds do not damage LEXAN polycarbonate brand polycarbonate used as windshield components, MYLAR polyester, the silicone seal of such windshields, the paint finish on the vehicles, or many decals.

Glycol ethers may be made by reacting alcohols and ethylene oxide in accordance with conventional methods. Glycol ethers also are widely available from a number of commercial sources. Specific examples include propylene glycol n-butyl ether (Dow Chemical Company), propylene glycol n-propyl ether (Dow Chemical Company), diethylene glycol monobutyl ether (Eastman Chemical Co.), ethylene glycol monobutyl ether (Eastman Chemical Co.), dipropylene glycol methyl ether, (Dow Chemical Company) propylene glycol methyl ether (Dow Chemical Company) combinations of these, and the like.

The cleaning composition of the present invention generally includes a sufficient amount of one or more degreasers such that the composition can satisfy the Oil Solubility Test described above. However, above a certain level, adding too much degreaser offers little additional benefit beyond that provided by lesser amounts. The enhanced cleaning power might also be detrimental to some inks and paints. The composition also might not be as user-friendly. Accordingly, preferred cleaning compositions of the present invention include 1 to 20, preferably 3 to 15, more preferably 5 to 10 parts by weight of the degreaser per 5 to 70, preferably 20 to 60, more preferably 35 to 50 parts by weight of the rubber solvent. A particularly preferred composition includes 6% to 10% by volume of at least one glycol ether as the degreaser.

The rubber solvent is a material that is capable of at least partially solubilizing rubber. The presence of the rubber solvent allows the cleaning composition to easily remove bits of rubber that may be stuck to surfaces such as race vehicle windshields, race vehicle bodies, race track walls, industrial floors, motorcycle windshields, and the like. This component is especially suitable for rapidly removing tire bits from race vehicle windshields during a pit stop.

A wide variety of rubber solvents are known and may be advantageously incorporated into cleaning compositions of the present invention. Preferred rubber solvents belong to the class of hydrocarbon solvents and may be aliphatic, aromatic, straight chain, branched, linear, and/or cyclic. The suitable hydrocarbon solvents may comprise one or more hetero atoms and be substituted or unsubstituted. Representative examples of rubber solvents include one or more of toluene, benzene, xylene, C5 to C15 paraffins, cycloparaffins, an olefin, acetylene polymers, terpene polymers, isoprene polymers, turpentine, petroleum products such as gasoline, kerosene, petroleum distillate, naphtha, mineral spirits, and the like; and natural and/or synthetic hydrocarbons and/or oils such as mineral oil, vegetable oil, animal oil, essential oil, edible oils, combinations of these, and the like. Specific oils include fish oil, sperm oil, fish-liver oil, corn oil, safflower oil, soybean oil, cottonseed oil, palm oil, coconut oil; combinations of these, and the like.

Although embodiments may be aromatic or aliphatic, aromatic rubber solvents tend to damage polycarbonate and other plastic surfaces. Accordingly, nonaromatic rubber solvents are preferred in those embodiments of the present invention to be used for cleaning polycarbonate or other plastic surfaces, e.g., race vehicle windshields. In this regard, a naphtha or naphtha derivative (collectively referred to as "naphtha" herein) is preferred.

Rubber solvents suitable in the practice of the present invention are widely available from a number of commercial sources. Representative examples of these include Exxon 2024 Naphtha (Exxon Chemical Company) Exxon Exxsol D115/145 Naphtha (Exxon Chemical Company), Exxon Isopar E fluid (Exxon Chemical Company), VM&P naphtha HT (Shell Chemical Company), Cypar-7 hydrocarbon solvent (Shell Chemical Company), Special Naphtholite 66/3 hydrocarbon solvent (Citgo Petroleum Corporation), Sol 340 HT hydrocarbon solvent (Shell Chemical Company), Soltrol 10 hydrocarbon solvent (Philips Chemical Company), Solvo-Kleen hydrocarbon solvent (NCH Corporation), Soltrol 70 (Phillips Chemical Company), combinations thereof, and the like.

The cleaning composition includes enough of the rubber solvent so that the composition has the desired level of rubber removing capabilities, but not so much that the cleaning composition leaves an undesirable residue on the surface being cleaned. Preferred cleaning compositions include 5 to 70, preferably 20 to 60, more preferably 35 to 50 parts by weight of the rubber solvent per 1 to 20 preferably 3 to 15, preferably 5 to 10 parts by weight of the degreaser.

The cleaning compositions also include one or more organic diluents. In the practice of the present invention, the diluent may be active, latent, or inactive. Active means that the diluent is a strong solvent for the soil being cleaned. Latent means that the diluent functions as an active solvent in the presence of one or both of the degreaser and/or rubber solvent. Inactive means that the diluent is a nonsolvent for the particular soil at issue, but may be present to help control viscosity, evaporation rate, or the like. As general guidelines, using 5 to 70, preferably 20 to 60, more preferably 35 to 50 parts by weight of the diluent is advantageously used per 5 to 70, preferably 20 to 60, more preferably 35 to 50 parts by weight of the rubber solvent.

The preferred organic diluent may be any solvent or combination of solvents that is capable of forming single phase mixtures with the rubber solvent and the degreaser. Preferred diluents comprise one or more nonaqueous, polar solvents. These preferred diluents include, for example, alcohols such as ethanol (typically denatured for this use), isopropyl alcohol (preferably at least 99% pure), combinations of these, and the like. Alcohols evaporate cleanly, are polar, are excellent wetting agents, and are typically latent or active solvents. Alcohols are also excellent carriers of carbon black, which is typically a constituent of the rubber residues that might be cleaned with the present invention. Accordingly, an alcohol may enhance the rubber cleaning performance of the cleaning composition. C2 to C5 alcohols are preferred, of which isopropyl alcohol and ethanol are most preferred. Isopropyl alcohol (IPA) provides exceptional cleaning performance, but may have a tendency to degrade some brands of decals used on race vehicle bodies. Ethanol is much more compatible with such decals and is therefore desirably used in applications in which the cleaning composition may come into contact with such decals. A combination of isopropanol and ethanol may be useful to obtain a good balance between optimum cleaning power and compatibility with decals. In such embodiments, the weight ratio of isopropanol to ethanol may be in the range from 1:19 to 19:1, preferably 1:4 to 4:1.

In addition to the degreaser, the rubber solvent, and the diluent, cleaning compositions may also include one or more additives that enhance the stability, performance, and/or handling of the cleaning composition. For example, other additives that might be used include antistatic agents, foaming agents, antioxidants, anticorrosion agents, fungicides, bactericides, fillers, pigments, combinations of these, and the like. If any of these are used, they may be used in accordance with conventional practices.

Cleaning compositions of the present invention are preferably water-restricted. It has been found that the presence of too much water not only may have a destabilizing effect upon the cleaning composition itself, but also may tend to impair cleaning performance. Accordingly, "water restricted" in the practice of the present invention means that the cleaning composition includes a low enough content of water such that the cleaning composition is a single phase at room temperature, and more preferably, remains a single phase at temperatures as low as 31° F. (0° C.). Preferred compositions contain less that 5%, preferably less than 1%, and more preferably less than 0.5% water. For purposes of determining water content, water that is in azeotropic combination with an alcohol or other constituent shall be deemed to be part of the aqueous content of the composition.

Preferred cleaning compositions of the present invention are also substantially free of surfactants, particularly in instances in which the cleaning composition is to be used to clean race vehicle windshields during the course of a race. Compositions that include surfactants have a tendency to leave a residue on the surface being cleaned, and this residue is relatively difficult to remove quickly in the timeframe of the typical pit stop. Such a residue is undesirable since it can impair the driver's visibility, posing a danger not only to the driver but to other racers, support crews, officials, and bystanders.

Cleaning compositions of the present invention are extremely easy to make and use. According to one approach of making the composition, the ingredients are combined in the desired proportions in a vessel and then stirred until the mixture is homogeneous. The ingredients can be combined in a batch or a continuous process. The mixture has a long shelf life and can be stored in a suitable storage container for very long periods of time. Alternatively, the mixture can be used relatively soon after it has been made.

To clean a soiled surface, the cleaning composition can be poured directly onto the surface, applied by cloth or sponge or other implement, sprayed, or the like. The cleaning composition will quickly loosen and/or dissolve oils, greases, rubber, tar, organic residues, particulate matter, and the like. If desired, the composition can be used to scrub the surface to remove especially stubborn soil, if desired. The composition and soil are then removed from the surface with a clean cloth, sponge, squeegee, or the like. The cleaning composition is particularly useful for cleaning race vehicle windshields, where fast cleaning action is paramount.

Other embodiments of the present invention may be formulated with ingredients that have higher flash points, e.g., are relatively less volatile, making such embodiments well suited for use in decontamination methodologies. The embodiments of the invention formulated from ingredients having higher flash points are also suitable for cleaning dirt, grease, paint, stain, oil, and other grime from the hands or other body surfaces. In the practice of the present invention, such embodiments are preferably formed ingredients comprising a degreaser compound, a rubber solvent, and an organic, polar diluent, wherein at least one, more preferably at least two, and most preferably at least all three of such ingredients have a flash point of at least 30° C., preferably at least about 50° C., and more preferably at least about 65° C.

Representative examples of polar organic diluents having high flash points include iso-hexanol (flash point of 145° F.; boiling point of 304° F.); n-hexanol (flash point of 142° F.; boiling point of 313° F.); and other alcohols having at least about 5, more preferably at least about 6 carbon atoms.

Representative examples of hydrocarbon solvents with higher flash points preferably are those that are aliphatic and/or are hydro-treated such as CITGO 142 Solvent 66/3 8052-41-3 (flash point of 145° F.; boiling point of 378° F.); CITGO Mineral Spirits 150 66/3 8052-41-3 (flash point of 154° F.; boiling point of 384° F.); SHELL Sol 142 HT 64742-88-7 (flash point of 145° F.; boiling point of 370° F.); EXXSOL D 60 64742-47-8 (flash point of 145° F.; boiling point of 370° F.); EXXSOL D 80 64742-47-8 (flash point of 180° F.; boiling point of 406° F.); and EXXSOL D 95 64742-47-8 (flash point of 206° F.; boiling point of 435° F.). CITGO brand solvents are available from Citgo Petroleum Corp. EXXSOL brand solvents are available from Exxon Mobil Corporation. SHELL brand solvents are available from the Shell Oil Company.

Specific examples of higher flash point degreaser compounds include glycol ether compounds such as propylene glycol butyl ether (flash point of 145° F.; boiling point of 340° F.); dipropylene glycol butyl ether (flash point of 212°

F.; boiling point of 446° F.); and tripropylene glycol butyl ether (flash point of 259° F.; boiling point of 525° F.).

Representative embodiments of cleaner compositions with higher flash point ingredients include the following: 1 to 20 parts by weight of the degreaser per 5 to 70 parts of the rubber solvent and 5 to 70 parts by weight of diluent per 5 to 70 parts by weight of the rubber solvent.

Formulation 1: 5 to 70, preferably about 30 parts by weight of hexanol; 1 to 20, preferably about 10 parts by weight of dipropylene glycol butyl ether; 5 to 70, preferably about 60 parts by weight of hydrocarbon solvent such as EXXSOL D 60, EXXSOL D 80, and/or EXXSOL D 95.

Formulation 2: 5 to 70, preferably about 30 parts by weight of hexanol; 1 to 20, preferably about 10 parts by weight of tripropylene glycol butyl ether; and 5 to 70, preferably about 60 parts by weight of hydrocarbon solvent such as EXXSOL D 60, EXXSOL D 80, and/or EXXSOL D 95.

In a practical test, a cleaner composition having higher flash point ingredients was used to clean a more than fifty year-old engine component having years of grease and grime built up. The cleaner easily removed the grease and grime, leaving the component very clean after the treatment.

The cleaning composition would be very useful to help decontaminate surfaces. The compositions may be used in one stage treatments in which a contaminated material is contacted with the cleaning composition by itself or in combination with one or more other decontaminating compositions. In other modes of practice, the compositions may be used in multiple stage treatments in which at least one of the stages involves contacting a contaminated material with the cleaning compositions by itself or in combination with one or more other compositions.

In many instances, a contaminated surface may not only be contaminated with hazardous materials, but it also might be wholly or partially covered with grease, grime, oil, dirt, paint, stain, or other residue. In such instances a preferred mode of practice involves at least two cleaning steps. In one step, the contaminated and dirty material is first contacted with a degreaser composition of the present invention. This removes the grease, grime, oil, dirt, paint, stain, or other residue, better exposing the underlying material to further treatment. In another step, the contaminated material is contacted with at least one additional cleaning composition. The additional cleaning composition(s) may be acidic, basic, oxidizing, reducing, and/or the like. In preferred embodiments the at least one additional cleaning composition comprises an acidic etching composition when the surfaces being decontaminated containing metal surfaces.

The present invention will now be further described with reference to the following examples.

EXAMPLE ONE

This test involved placing in a clear plastic cup or a clear glass jar about 2 ounces (59 ml) cup pure chemical or cleaner: full strength for pure chemicals and ready-to-use cleaners, or diluted as directed by the manufacturer for concentrated cleaners. Two to three drops of 20W–50 racing motor oil were dropped into this liquid. The immediate effect of the liquid on the oil was recorded: for example, if the oil immediately began to dissolve in the liquid. The liquid and oil drops were then stirred and the effect of this stirring on the oil was recorded: the stirring simulated any agitation from applying the liquid to a surface (e.g., scraping with a squeegee or a cloth). Then, after waiting three to four minutes, the characteristics of the liquid and oil combination were recorded again. This waiting ascertained if the liquid affected the oil to a greater extent over a greater period of time and if the dissolved oil stayed dissolved over a greater period of time. Any liquid that had a greater dissolution effect on the oil in any of these three situations was a better solvent for the oil.

The first group tested with this method included plain water for comparison and 45 existing cleaners, some sold for home use and some sold for industrial/commercial use. Testing with this group showed that, after ruling out cleaners with surfactants because they leave a residue, glycol ethers were the best solvents for dissolving oils. This test also showed that certain hydrocarbon solvents and diluents could contribute oil-dissolving prowess to a cleaning composition. The tested cleaners and the test results are displayed in this table.

| | EXAMPLE ONE: Does Oil Dissolve in Cleaner . . . | | |
|---|---|---|---|
| CLEANER | Immediately without Stirring? | Immediately with Stirring? | After a Few Minutes? |
| 409* | No | Yes | Yes |
| ammonia | No | Somewhat | No |
| BK Blue All-Purpose Cleaner | No | No | No |
| BK Window Cleaner Concentrate | No | No | Somewhat |
| Comet Bathroom Cleaner* | No | Yes | Yes |
| Dawn | Somewhat | Yes | Yes |
| Easy-Off degreaser | No | Somewhat | Yes |
| Easy Paks All-Purpose Cleaner/ Deodorizer | Somewhat | Yes | Yes |
| Easy Paks/Mr. Muscle Heavy-Duty Cleaner Degreaser | Somewhat | Somewhat | Yes |
| Easy Paks Neutral Cleaner | Somewhat | Yes | Yes |
| Fantastik* | No | Yes | Yes |
| Glance glass cleaner* | foamy spray so couldn't tell effect on oil | Somewhat | Somewhat |
| Grayline WM-Wash printing press wash* | Yes | Yes; dissolved plastic container it was in | (not tested) |

-continued

| CLEANER | EXAMPLE ONE: Does Oil Dissolve in Cleaner . . . Immediately without Stirring? | Immediately with Stirring? | After a Few Minutes? |
|---|---|---|---|
| Heavyweight degreaser* | Somewhat | Yes | Yes |
| HFE-7100 | Yes (dissolved plastic container) | (not tested) | (not tested) |
| Lestoil | No | Somewhat | No |
| Mr. Clean-Top Job | No | Yes | Yes |
| Multi-Clean Eliminator* | Yes | Yes | Yes |
| Murphy's Kitchen Care All-Purpose Cleaner* | Yes | Yes | Yes |
| Murphy's Kitchen Care Glass & Surface Spray* | Somewhat | Yes | Yes |
| Murphy's Oil Soap-Liquid | Yes | Yes | Yes |
| Pledge Wood Cleaner* | No | Yes | No |
| Revlon Nail Enamel Remover (w. no acetone) | No | Somewhat | (not tested) |
| Rust-Oleum Pure Strength | Somewhat | Yes | Somewhat |
| SD-20* | foamy so couldn't tell effect on oil | Somewhat; still foamy so couldn't tell effect on oil very accurately | Somewhat; still foamy so couldn't tell effect on oil very accurately |
| Simple Green* | Somewhat | Somewhat | Yes |
| Simple Green Industrial Cleaner and Degreaser* | No | Somewhat | Yes |
| Simple Green Crystal Industrial Degreaser* | Somewhat | Somewhat | Yes |
| Soilax | No | Yes | Somewhat |
| Tough Duty* | No | Yes | (not tested) |
| Vertrel KCD-9545 | Somewhat | Yes | (not tested) |
| Vertrel KCD-9548 | No | Somewhat | (not tested) |
| Vertrel KCD-9550 | No | Somewhat | (not tested) |
| Vertrel SMT | Yes | Yes | (not tested) |
| Vertrel XM | No | Somewhat | (not tested) |
| vinegar | Somewhat | Somewhat | No |
| water | No | (not tested) | (not tested) |
| Whistle All-Purpose Cleaner with ammonia* | foamy spray so couldn't tell effect on oil | Somewhat; foamy spray so couldn't tell effect on oil accurately | Somewhat |
| Windex-blue* | No | Yes | Somewhat |
| Windshield Washer Fluid | No | Somewhat | Somewhat |
| Zep Big Orange | Somewhat | Yes; dissolved plastic container it was in | (not tested) |
| Zep I. D. Orange Liquid* | Yes | Yes | Yes |
| Zep Powerhouse* | No | Yes | No |
| Zepride* | Yes | Yes | No |
| Zep Vue - Glass Cleaner* | No | Yes | Somewhat |

*= contains a glycol ether

The results of testing 17 pure chemicals with the method of Example One are found in the following table. In this testing, the PnB and PnP glycol ethers were shown to be better oil solvents than the DB and EB glycol ethers. Because of this and the fact that DB evaporated too slowly and EB produced particulate matter, PnB and PnP are preferred. The siloxane was also eliminated because of particulate matter.

| CHEMICAL | EXAMPLE ONE: Does Oil Dissolve in Chemical . . . Immediately without Stirring? | Immediately with Stirring? | After a Few Minutes? |
|---|---|---|---|
| Commercial Alcohols ethyl alcohol - anhydrous (ethanol) | No | Somewhat | (not tested) |
| Condea Vista Alfol C6 alcohol (hexanol) | No | Yes | (not tested) |
| Dow Corning OS-10 siloxane (OS-10 siloxane) | No | Yes | A particulate like a coarse powder formed in bottom of container |
| Dow propylene glycol n-butyl ether (PnB) | Oil started to dissolve | Yes; dissolved a little more quickly than in EB | Yes |

-continued

| CHEMICAL | EXAMPLE ONE: Does Oil Dissolve in Chemical . . . Immediately without Stirring? | Immediately with Stirring? | After a Few Minutes? |
|---|---|---|---|
| Dow propylene glycol n-propyl ether (PnP) | Oil started to dissolve | Yes | Yes |
| drugstore isopropanol-91% (isopropanol-91%) | No | Yes | No; oil sunk to bottom of container |
| Eastman diethylene glycol monobutyl ether (DB) | Oil floated on top of DB | Yes | A small amount of oil was not dissolved |
| Eastman ethylene glycol monobutyl ether (EB) | Oil floated on top of EB and became threadlike | Yes | Golden reddish-brown curds formed in the EB |
| Exxon 2024 Naphtha hydrocarbon solvent (2024 Naphtha) | No | needed at least 5 to 10 seconds of agitation to dissolve | Yes |
| Exxon Exxsol D115/145 Naphtha hydrocarbon solvent (Exxsol D115/145) | Oil started to dissolve | Yes | (not tested) |
| Exxon Isopar E hydrocarbon solvent (Isopar E) | No | Yes | (not tested) |
| hardware store acetone (acetone) | No | Somewhat | (not tested) |
| isopropanol 91% | No | Yes | No |
| NCH Solvo-Kleen hydrocarbon solvent (Solvo-Kleen) | No | Yes | (not tested) |
| Shell Cypar-7 hydrocarbon solvent (Cypar-7) | No | needed at least 5 to 10 seconds of agitation to dissolve | Yes |
| Shell VM&P Naphtha HT hydrocarbon solvent (VM&P HT) | No | Yes | (not tested) |
| Sunnyside Mineral Spirits (mineral spirits) | No | Yes | (not tested) |

This test was also done with a heavier oil, 80W–90 gear oil, that was dropped into a container of 100% PnB. This test demonstrated that glycol ethers could dissolve a heavier oil as well as the lighter oil used in the testing above.

EXAMPLE TWO

In this test, about 0.5 teaspoons of 20W–50 racing motor oil was poured onto and then smeared over one side of a 6-inch square of LEXAN polycarbonate. (LEXAN polycarbonate is an example of a plastic that can be damaged easily by numerous chemicals.) Then, either a pure chemical, a ready-to-use cleaner, or a concentrated cleaner that had been diluted as directed by the manufacturer was applied to the surface. The surface was wiped with a white paper towel using a moderate amount of effort. The effect of this cleaning action was recorded. Without smearing any more oil over the LEXAN polycarbonate surface, that is, leaving the surface as it was after the first cleaning attempt, the liquid was applied to the surface a second time, and the surface was wiped with a white paper towel. The effect of this second cleaning action was recorded.

The first group tested with the method of Example Two included 37 existing mixtures used as cleaners, some sold for home use and some sold for industrial/commercial use. This first testing group revealed which chemicals cleaned oil from a chemically sensitive plastic surface the most effectively. As in Example One, cleaners with glycol ethers performed very well overall in this test. Several cleaners with surfactants also performed very well in this test, but they usually left a slight or obvious residue on the surface.

In addition, the test results from this first group confirmed what the technical literature stated, which is that LEXAN polycarbonate can be damaged or left with a vision-obscuring residue by certain chemicals: sodium metasilicate, d-limonene, halogenated hydrocarbons, aromatic hydrocarbons, ketones, and surfactants, among others. One or more of all of these certain chemicals can be found in several of the cleaners tested. Such cleaners often did clean an oily surface very well, but too often produced the predicted damage or residue.

The results from this first group then are in the following table.

| CLEANER | How did the cleaner clean an oily surface? |
|---|---|
| 409* | Very well. |
| Acetone | Clouded surface. |
| ammonia | Didn't clean surface. |
| BK Blue All-Purpose Cleaner | Well. |
| Dawn dishwashing liquid | Well. |
| Easy Paks All-Purpose Cleaner/Deodorizer | Well. |
| Easy Paks Neutral Cleaner | Well. |
| Easy Paks/Mr. Muscle Heavy-Duty Cleaner Degreaser | Well. |
| Easy-Off degreaser | Very well. |
| Fantastik* | Very well. |
| Glance glass cleaner* | Very well. |
| Grayline WM-Wash printing press wash* | Very well. |
| Heavyweight degreaser* | Well. |
| HFE-7100 | Well. |
| Mr. Clean-Top Job | Left cloudy residue. |
| Multi-Clean Eliminator* | Very well. |
| Murphy's Kitchen Care All-Purpose Cleaner* | Very well. |
| Murphy's Kitchen Care Glass & Surface Spray* | Very well. |
| Murphy's Oil Soap - Liquid | Well. |
| Pledge Wood Cleaner* | Well. |
| Revlon Nail Enamel Remover | Very well. |
| Rust-Oleum Pure Strength | Left cloudy residue. |

-continued

| CLEANER | How did the cleaner clean an oily surface? |
|---|---|
| SD-20* | Very well. |
| Simple Green* | Well. |
| Solvo-Kleen | Very well. |
| Tough Duty | Very well. |
| Vertrel KCD-9545 | Very well. |
| Vertrel KCD-9548 | Very well. |
| Vertrel KCD-9550 | Very well. |
| Vertrel SMT | Very well. |
| Vertrel XM | Very well. |
| Whistle All-Purpose Cleaner with ammonia* | Very well. |
| Windex - blue* | Very well. |
| Windshield Washer Fluid | Very well. |
| Zep I. D. Orange Liquid* | Very well. |
| Zep Powerhouse* | Very well. |
| Zep Vue - Glass Cleaner* | Very well. |
| Zepride* | Well. |

*= contains a glycol ether

Another group tested with this method included mixtures of each of the following 17 cleaners or chemicals mixed in a 50-50 ratio by volume (Note: all ratios expressed throughout this specification and in the claims are by volume unless otherwise noted) with hardware store naphtha. These 17 were chosen for this test because they performed well in Examples One and Two above and because they had no chemical components which damage LEXAN polycarbonate or leave a residue on LEXAN polycarbonate. The naphtha was chosen because it proved to be a good rubber solvent in the tests of Example Three. The testing here showed that adding naphtha did not reduce the effectiveness of these cleaners in removing oily soil.

| CLEANER MIXED WITH NAPHTHA IN A 50/50 RATIO | How did the cleaner plus naphtha clean the oily surface? |
|---|---|
| 409* | Very well. |
| BK Window Cleaner Concentrate | Too smeary. |
| drugstore isopropanol-99% (isopropanol) | Very well. |
| Fantastik* | Well. |
| Glance glass cleaner* | Very well. |
| Multi-Clean Eliminator* | Very well. |
| Murphy's Kitchen Care All-Purpose Cleaner* | Very well. |
| Murphy's Kitchen Care Glass & Surface Spray* | Very well. |
| Murphy's Oil Soap - Liquid | Very well. |
| Pledge Wood Cleaner* | Very well. |
| SD-20* | Very well. |
| Simple Green* | Well. |
| Whistle All-Purpose Cleaner with ammonia* | Very well. |
| Windex - blue* | Very well. |
| Windshield Washer Fluid | Very well. |
| Zep Powerhouse* | Very well. |
| Zep Vue - Glass Cleaner* | Very well. |

*= contains a glycol ether

Also tested with this method were mixtures that included each of the following 8 cleaners mixed in equal volume parts with hardware store naphtha and isopropanol. The naphtha was chosen because it proved to be a good rubber solvent in the testing of Example Three. The isopropanol was chosen because it cleaned oil well and proved to be a moderately effective rubber solvent in the testing of Example Three. The testing here showed that adding naphtha and isopropanol did not reduce the effectiveness of these cleaners in removing oily soil. The cleaners tested in these mixtures then were these:

| CLEANER MIXED WITH NAPHTHA AND ISOPROPANOL IN EQUAL MEASURES | How did the cleaner plus naphtha plus isopropanol clean the oily surface? |
|---|---|
| BK Window Cleaner Concentrate | Too smeary. |
| Multi-Clean Eliminator | Very good. |
| Murphy's Kitchen Care All-Purpose Cleaner | Very good. |
| Murphy's Kitchen Care Glass & Surface Spray | Very good. |
| Murphy's Oil Soap - Liquid | Very good. |
| SD-20 | Very good. |
| Windshield Washer Fluid | Very good. |
| Zep Vue - Glass Cleaner | Very good. |

Also tested with this method were the following pure chemicals. This group is representative of the components in the above cleaners that cleaned an oily surface very well with no damage or residue. As this test proved, each component alone also cleaned an oily surface very well with no damage or residue.

| CHEMICAL | How did the chemical clean an oily surface? |
|---|---|
| 2024 Naphtha | Well. |
| Citgo Special Naphtholite 66/3 hydrocarbon solvent (Naphtholite) | Very well. |
| Commercial Alcohols Specially Denatured Alcohol 3C Anhydrous (denatured ethanol) | Very well. |
| Cypar-7 | Well. |
| ethanol | Very well. |
| Exxsol D115/145 | Very well. |
| Isopar E | Very well. |
| isopropanol | Very well. |
| isopropanol-91% | Very well. |
| mineral spirits | Very well. |
| Phillips Soltrol 70 hydrocarbon solvent (Soltrol 70) | Very well. |
| PnB | Very well. |
| PnP | Very well. |
| Solvo-Kleen | Very well. |
| VM&P HT | Very well. |

Several mixtures of pure chemicals were tested using this Example Two method. Some mixtures with EB and 2024 Naphtha or including an anti-static agent left a film. In other mixtures, replacing part of the isopropanol with ethanol did not reduce the effective cleaning power of the mixture. Different proportions of PnB and PnP were effective, too. The results of these tests combined with the results of the tests in Example Three provided insight into the optimal components to include in a preferred cleaning mixture. The mixtures tested were as follows:

| MIXTURE | How did the mixture of chemicals clean an oily surface? |
|---|---|
| 5% EB, 5% PnB, 25% 2024 Naphtha, 65% isopropanol | Very well. |
| 5% EB, 5% PnB, 50% 2024 Naphtha, 40% isopropanol | Very well, but left film. |
| 5% PnB, 5% PnP, 5% Cypar-7, 85% isopropanol | Very well. |
| 5% PnB, 5% PnP, 5% mineral spirits, 85% isopropanol | Well; not as good as a mixture with more mineral spirits. |

-continued

| MIXTURE | How did the mixture of chemicals clean an oily surface? |
|---|---|
| 5% PnB, 5% PnP, 25% Cypar-7, 2.5% Croda Crodastat 100 quatenary ammonium chloride (anti-static agent), 62.5% isopropanol | Left a bad residue. |
| 5% PnB, 5% PnP, 25% Cypar-7, 10% OS-10 siloxane, 55% isopropanol | Very well. |
| 5% PnB, 5% PnP, 25% Cypar-7, 65% isopropanol | Very well. |
| 5% PnB, 5% PnP, 25% Isopar E, 32.5% ethanol, 32.5% isopropanol | Very well. |
| 5% PnB, 5% PnP, 25% Isopar E, 65% isopropanol | Very well. |
| 5% PnB, 5% PnP, 25% mineral spirits, 65% isopropanol | Very well. |
| 5% PnB, 5% PnP, 40% Exxsol D115/145, 25% ethanol, 25% isopropanol | Very well. |
| 5% PnB, 5% PnP, 40% Isopar E, 25% ethanol, 25% isopropanol | Very well. |
| 5% PnB, 5% PnP, 40% VM&P HT, 25% ethanol, 25% isopropanol | Very well. |
| 10% EB, 25% 2024 Naphtha, 65% isopropanol | Very cloudy; left film. |
| 33% PnB, 67% PnP | Very well. |
| 50% PnB, 50% PnP | Very well. |
| 67% PnB, 33% PnP | Very well. |

This test was also done with heavier oil, 80W–90 gear oil, spread over a LEXAN polycarbonate square and cleaned with a mixture of 50% PnB and 50% PnP. This test showed that glycol ethers can clean a LEXAN polycarbonate square coated with heavier oil as well as it cleans one coated with lighter oil.

EXAMPLE THREE

In this test, a pure chemical, a ready-to-use cleaner, or a concentrated cleaner that had been diluted as directed by the manufacturer was poured on a paper towel. The towel was rubbed over the outer surface of a rubber racing tire. A record was made of the appearance of the paper towel: whether the towel had tire rubber on it which would indicate whether or not the liquid dissolved tire rubber, and how dark or light was any rubber residue on the towel, which would indicate the extent to which the liquid dissolved tire rubber.

The first group tested with this method included 41 existing cleaners, some sold for home use and some sold for industrial/commercial use. This test first showed in a general way that alcohols and aromatic and aliphatic hydrocarbon solvents were most effective at dissolving rubber. The cleaners tested were as follows.

| CLEANER | Can the cleaner dissolve tire rubber? |
|---|---|
| 409 | Somewhat. |
| ammonia | No. |
| BK Blue All-Purpose Cleaner | No. |
| Dawn dishwashing liquid | No. |
| Easy Paks All-Purpose Cleaner/Deodorizer | No. |
| Easy Paks Neutral Cleaner | No. |
| Easy Paks/Mr. Muscle Heavy-Duty Cleaner Degreaser | No. |
| Easy-Off degreaser | No. |
| Fantastik/full | No. |
| Glance glass cleaner | Somewhat. |
| Grayline WM-Wash printing press wash | Very well. |

-continued

| CLEANER | Can the cleaner dissolve tire rubber? |
|---|---|
| Heavyweight degreaser | No. |
| HFE-7100 | Very well. |
| Mr. Clean-Top Job | No. |
| Multi-Clean Eliminator | No. |
| Murphy's Kitchen Care All-Purpose Cleaner | No. |
| Murphy's Kitchen Care Glass & Surface Spray/ | No. |
| Murphy's Oil Soap - Liquid | No. |
| Pledge Wood Cleaner | No. |
| Rain-X | Well. |
| Revlon Nail Enamel Remover | Well. |
| Rust-Oleum Pure Strength | No. |
| SD-20 | No. |
| Simple Green | No. |
| Simple Green Crystal Industrial Degreaser | No. |
| Simple Green Industrial Cleaner and Degreaser | No. |
| Solvo-Kleen/full | Well. |
| Tough Duty | No. |
| Vertrel KCD-9545 | Well. |
| Vertrel KCD-9548 | Somewhat. |
| Vertrel KCD-9550 | Well. |
| Vertrel SMT | Very well. |
| Vertrel XM | Somewhat. |
| WD-40 | Well. |
| Whistle All-Purpose Cleaner with ammonia | No. |
| Windex - blue | No. |
| Windshield Washer Fluid | No. |
| Zep I. D. Orange Liquid | Yes. |
| Zep Powerhouse | No. |
| Zep Vue - Glass Cleaner | No. |
| Zepride | No. |

Another group tested with this method included mixtures of each of the following 17 cleaners or chemicals mixed in a 50-50 ratio with hardware store naphtha. This testing showed that adding a hydrocarbon solvent to a cleaner produced a mixture that was better at dissolving rubber than the cleaner alone was.

| CLEANER MIXED WITH NAPHTHA IN A 50/50 RATIO | Can the cleaner plus naphtha dissolve tire rubber? [Comment on left.] | From table just above: Can the cleaner alone dissolve tire rubber? [Comment on right.] |
|---|---|---|
| 409 | Somewhat. | Somewhat. |
| BK Window Cleaner Concentrate | Somewhat. | (not tested) |
| Fantastik | No. | No. |
| Glance glass cleaner | Somewhat. | Somewhat. |
| isopropanol | Well. | (not tested) |
| Multi-Clean Eliminator | Well. | No. |
| Murphy's Kitchen Care All-Purpose Cleaner | Somewhat. | No. |
| Murphy's Kitchen Care Glass & Surface Spray | Somewhat. | No. |
| Murphy's Oil Soap - Liquid | Somewhat. | No. |
| Pledge Wood Cleaner | Somewhat. | No. |
| SD-20 | Well. | No. |
| Simple Green | Somewhat. | No. |
| Whistle All-Purpose Cleaner with ammonia | Somewhat. | No. |
| Windex - blue | Somewhat. | No. |
| Windshield Washer Fluid | Well. | No. |
| Zep Powerhouse | Well. | No. |
| Zep Vue - Glass Cleaner | Well. | No. |

This method was also used to test mixtures that included each of the following 8 cleaners in the next table. To make each mixture, the cleaner, hardware store naphtha, and isopropanol (all isopropanol is 99% pure isopropanol obtained from a pharmacy retailer unless otherwise noted) were stirred together in equal parts. This testing showed that adding both a hydrocarbon solvent and an alcohol to an existing cleaner produced a mixture that was better at dissolving rubber than either the cleaner alone was or the cleaner plus a hydrocarbon solvent was.

The cleaners tested in the mixtures with naphtha and isopropanol were these:

| CLEANER MIXED WITH NAPHTHA AND ISOPROPANOL IN EQUAL MEASURES | Can the cleaner plus naphtha plus isopropanol dissolve tire rubber? [Comment on left.] | From table just above: Can the cleaner plus naphtha dissolve tire rubber? [Comment on right.] |
|---|---|---|
| BK Window Cleaner Concentrate | Somewhat. | Somewhat |
| Multi-Clean Eliminator | Well. | Well |
| Murphy's Kitchen Care All-Purpose Cleaner | Well. | Somewhat |
| Murphy's Kitchen Care Glass & Surface Spray | Well. | Somewhat |
| Murphy's Oil Soap - Liquid | Well. | Somewhat |
| SD-20 | Well. | Well |
| Windshield Washer Fluid | Well. | Well |
| Zep Vue - Glass Cleaner | Well. | Well |

After the testing of Example Eight exposed the problem of incorporating too much water into a cleaning mixture, several pure chemicals were tested using the method of Example Three. The results are shown in the next table. In particular, these tests showed which of the hydrocarbons were the best rubber solvents.

| CHEMICAL | Can the chemical dissolve tire rubber? |
|---|---|
| 2024 Naphtha | Well. |
| Acetone | Well. |
| Cypar-7 | Very well. |
| denatured ethanol | Somewhat. |
| Dow Corning OS-120 siloxane | Somewhat. |
| Dow Corning OS-20 siloxane | Somewhat. |
| Dow Corning OS-30 siloxane | Somewhat. |
| Eastman Texanol ester alcohol | Somewhat. |
| Eastman TXIB plasticizer | Somewhat. |
| Ethanol | Somewhat. |
| Exxsol D115/145 | Very well. |
| Isopar E | Very well. |
| isopropanol | Well. |
| isopropanol-91% | Somewhat. |
| Mineral spirits | Very well. |
| OS-10 siloxane | Somewhat. |
| PnB | Well. |
| PnP | Well. |
| Soltrol 70 | Well. |
| Solvo-Kleen | Very well. |
| Special Naphtholite | Very well. |
| VM&P HT | Very well. |

Several mixtures of pure chemicals were tested using the method of Example Three. These tests showed that the more effective mixtures contained ethanol and higher percentages of hydrocarbon solvent. In addition, these tests support the conclusion that, because none of the tested existing cleaners has the combination of a degreaser for removing oily soil and both a hydrocarbon solvent and an alcohol for removing rubber, none of the tested existing cleaners is as effective at removing both oily/greasy soil and rubber as a mixture comprising a degreaser, hydrocarbon solvent, and alcohol would be.

It should be noted that the existing cleaners tested here were selected from the cleaning products offered by 40 manufacturers. The great majority of those cleaning products were immediately recognizable as being inappropriate choices for solving this cleaning problem associated with soiled race vehicles. Thus, the group of existing cleaners tested here was not chosen at random, but was carefully assembled in a thorough effort to ascertain if there even was an existing cleaner that would contain a highly effective combination of chemicals for solving this cleaning problem. All of the Examples here (and the tests of Example Three in particular) show that such a highly effective combination should contain a degreaser, hydrocarbon solvent, and alcohol, but no existing cleaner with this combination was discovered during the extensive selection process described above. Therefore, there is obviously a need to construct a new mixture to solve this cleaning problem.

The chemicals tested were as follows:

| MIXTURE | Can the mixture of chemicals dissolve tire rubber? |
|---|---|
| 3% PnB, 3% PnP, 44% VM&P HT, 50% ethanol | Very well. |
| 4% PnB, 2% PnP, 54% Isopar E, 40% ethanol | Very well. |
| 5% EB, 5% PnB, 25% 2024 Naphtha, 65% isopropanol | Well. |
| 5% EB, 5% PnB, 50% 2024 Naphtha, 40% isopropanol | Well. |
| 5% PnB, 5% PnP, 5% Cypar-7, 85% isopropanol | Very well, but not as good as mixture with 25% Cypar-7. |
| 5% PnB, 5% PnP, 5% mineral spirits, 85% isopropanol | Somewhat, definitely not as good as with 25% mineral spirits. |
| 5% PnB, 5% PnP, 25% Cypar-7, 2.5% anti-static, 62.5% isopropanol | Very well. |
| 5% PnB, 5% PnP, 25% Cypar-7, 10% OS-10 siloxane, 55% isopropanol | Very well. |
| 5% PnB, 5% PnP, 25% Cypar-7, 65% isopropanol | Very well. |
| 5% PnB, 5% PnP, 25% Isopar E, 32.5% ethanol, 32.5% isopropanol | Well. |
| 5% PnB, 5% PnP, 25% Isopar E, 65% isopropanol | Well. |
| 5% PnB, 5% PnP, 25% mineral spirits, 65% isopropanol | Very well. |
| 5% PnB, 5% PnP, 40% Exxsol D115/145, 25% ethanol, 25% isopropanol | Well. |
| 5% PnB, 5% PnP, 40% Isopar E, 25% ethanol, 25% isopropanol | Well. |
| 5% PnB, 5% PnP, 40% VM&P HT, 25% ethanol, 25% isopropanol | Well. |
| 5% PnB, 5% PnP, 40% VM&P HT, 50% ethanol | Very well. |
| 10% EB, 25% 2024 Naphtha, 65% isopropanol | Well. |
| 10% PnB, 24% Special Naphtholite, 40% ethanol, 26% water | Somewhat. |
| 10% PnB, 30% VM&P HT, 60% ethanol | Well. |
| 10% PnB, 40% VM&P HT, 50% ethanol | Very well. |
| 10% PnB, 50% VM&P HT, 40% ethanol | Very well. |
| 10% PnB, 60% VM&P HT, 30% ethanol | Very well; the best of the combinations with varying amounts of ethanol. |

-continued

| MIXTURE | Can the mixture of chemicals dissolve tire rubber? |
|---|---|
| 40% isopropanol, 60% water | Didn't remove any rubber. |
| 50% Cypar-7, 50% OS-10 siloxane | Somewhat; addition of OS-10 did not increase solvency power. |
| 50% isopropanol, 50% water | Somewhat. |

EXAMPLE FOUR

In this test, a pure chemical, a ready-to-use cleaner, or a concentrated cleaner that had been diluted as directed by the manufacturer was poured into a glass jar to a depth of about one inch. A one-inch LEXAN polycarbonate square was placed in the liquid in the jar. The jar lid was screwed onto the jar snugly. After 24 hours, the LEXAN polycarbonate square was removed from the jar. The appearance and condition of the square (e.g., etching, cloudiness, de-laminating, cracking) were recorded.

This test indicated which chemicals might, over a long-term exposure, damage LEXAN polycarbonate which is used in race vehicle windshields and which is a very chemically sensitive plastic.

The liquids tested with this method included these:

| CHEMICAL/CLEANER | Does the chemical/cleaner damage LEXAN polycarbonate in a long-term exposure? |
|---|---|
| Energine Spot Remover | No. |
| Grayline WM-Wash printing press wash | No. |
| isopropanol | No. |
| Solvo-Kleen | No. |
| Vertrel SMT | Yes. |
| Xylol | Yes; contains aromatic hydrocarbon. |
| Zep I. D. Orange Liquid | No. |
| Zepride | Yes; contains sodium metasilicate. |

EXAMPLE FIVE

In this test, a lump of Loctite Permatex Silicone Windshield and Glass Seal #65A (a silicone sealant used around the edge of a LEXAN polycarbonate windshield) was squeezed onto a one-inch square of LEXAN polycarbonate. The lump was allowed to cure for at least 24 hours. The one-inch LEXAN polycarbonate square with the silicone lump was placed in a glass jar with a lid. A pure chemical, a ready-to-use cleaner, or a concentrated cleaner that had been diluted as directed by the manufacturer was poured into the jar and the jar lid was screwed onto the jar snugly. After 10 minutes, the appearance of the silicone was recorded. After 24 hours, the LEXAN polycarbonate square was removed from the jar; the appearance of the silicone was recorded. The silicone was prodded with a toothpick and the result recorded.

This test indicated which of the liquids listed in the next paragraph damage the silicone sealant used around race vehicle windshields.

The liquids tested with this method included the following:

| CHEMICAL/CLEANER | Does the chemical/cleaner damage silicone sealant in a short-term exposure? | Does the chemical/cleaner damage silicone sealant in a long-term exposure? |
|---|---|---|
| Energine Spot Remover | (not tested) | Yes; contains naphtha; damage was small. |
| Grayline WM-Wash printing press wash | No. | Yes; contains aromatic hydrocarbons; damage was significant. |
| isopropanol | No. | No. |
| Solvo-Kleen | No. | Yes; damage was small. |
| Vertrel SMT | No. | Yes; damage was moderate. |
| Xylol | (not tested) | Yes; contains an aromatic hydrocarbon; badly damaged. |
| Zep I. D. Orange Liquid | No. | Yes; badly damaged. |
| Zepride | (not tested) | No. |

EXAMPLE SIX

In this test, a pure chemical or a ready-to-use cleaner was applied to the painted body of a car. After three or four seconds, the liquid was wiped off with a terrycloth towel. The effect of the liquid on the paint was recorded.

This test showed which of the liquids listed in the next paragraph damage the paint on a car body.

The liquids tested with this method were these:

| CHEMICAL/CLEANER | Did the chemical/cleaner damage the car body's paint? |
|---|---|
| Grayline WM-Wash printing press wash | No. |
| isopropanol | No. |
| Solvo-Kleen | No. |
| Vertrel SMT | No. |
| Zep I. D. Orange Liquid | No. |

EXAMPLE SEVEN

Because carbon black is a substantial component of rubber tires and is "quasi-graphitic", marks were made on a plastic surface with pencil lead. A pure chemical was poured on the marks. The immediate effect of the liquid was recorded. The marks were wiped with a paper towel. The effect of the liquid on the marks was recorded.

This test showed which chemicals might be included in a formulation to help dissolve carbon black.

The liquids tested with this method included ethanol, hexanol, isopropanol, and hardware store naphtha. The ethanol, hexanol, and isopropanol dissolved the pencil lead better than the naphtha.

EXAMPLE EIGHT

In this test, a pure chemical or a ready-to-use cleaner or a concentrated cleaner that had been diluted as directed by the manufacturer was mixed with naphtha in a 50-50 volume ratio by stirring the cleaner and the naphtha together. The following were recorded: whether the cleaner and the naphtha stayed together as a mixture or whether they separated, and how long it took for any separation to occur.

This test showed which specific chemicals were immiscible with naphtha which was one of the rubber solvents being considered for inclusion in a preferred mixture. Such immiscible cleaners would be excluded from the preferred mixture. Because almost all of the cleaners had substantial percentages of water in them, they were immiscible with naphtha, which is a hydrophobic hydrocarbon solvent.

The 17 cleaners tested in these mixtures were these.

| CLEANER MIXED WITH NAPHTHA IN A 50/50 RATIO | Did the cleaner separate from the naphtha? |
|---|---|
| 409 | Yes. |
| BK Window Cleaner Concentrate | Yes. |
| Fantastik | Yes. |
| Glance glass cleaner | Yes. |
| isopropanol | No. |
| Multi-Clean Eliminator | Yes. |
| Murphy's Kitchen Care All-Purpose Cleaner | Yes. |
| Murphy's Kitchen Care Glass & Surface Spray | Yes. |
| Murphy's Oil Soap - Liquid | Yes. |
| Pledge Wood Cleaner | Yes. |
| SD-20 | Yes. |
| Simple Green | Yes. |
| Whistle All-Purpose Cleaner with ammonia | Yes. |
| Windex - blue | Yes. |
| Windshield Washer Fluid | Yes. |
| Zep Powerhouse | Yes. |
| Zep Vue - Glass Cleaner | Yes. |

EXAMPLE NINE

The method of Example Two was used with the following chemicals and mixtures of chemicals. This test determined if an unwanted oily or watery residue or if no residue was left by the cleaning agent on the LEXAN polycarbonate surface.

The liquids and mixtures tested were as follows:

| CHEMICAL OR MIXTURE | Did the chemical or mixture of chemicals leave an oily or watery residue on a surface? |
|---|---|
| 2024 Naphtha | No. |
| anti-static | No. |
| Cypar-7 | No. |
| Eastman Texanol ester alcohol | No. |
| Eastman TXIB plasticizers | No. |
| isopropanol | No. |
| OS-10 siloxane | No. |
| PnB | No. |
| PnP | No. |
| | No. |
| 5% PnB, 5% PnP, 20% Cypar-7, 60% isopropanol, 10% OS-10 siloxane | Yes; took extra rubbing with drying cloth to remove a small oily residue. |
| 5% PnB, 5% PnP, 25% Cypar-7, 65% isopropanol | Yes; took extra rubbing with drying cloth to remove a small oily residue. |
| 10% PnB, 90% isopropanol | No. |
| 10% PnP, 90% isopropanol | No. |
| 33% Cypar-7, 67% isopropanol | No. |
| 33% OS-10 siloxane, 67% isopropanol | No. |

EXAMPLE TEN

The method of Example Two was used with PnB and PnP, except that MYLAR polyester was used in place of LEXAN polycarbonate. This test indicated that glycol ethers could clean an oily MYLAR polyester surface as well as they could clean an oily LEXAN polycarbonate surface.

EXAMPLE ELEVEN

In this test, decals used on Winston Cup race vehicles and two decals made with blue and red inks that have very low chemical resistance were tested for compatibility with various chemicals and mixtures of chemicals. A pure chemical or mixture of chemicals was poured onto a white paper towel. The paper towel was rubbed over the surface of a decal. The effect on the decal was recorded, including how much, if any, decal ink was removed and how many rubbings did it take to remove or damage the decal ink.

This test showed which chemicals and mixtures of chemicals caused the least amount of damage to decals of greatly varying chemical resistance. In particular, the alcohols at 100% concentration were much more damaging to decals than the glycol ethers or hydrocarbon solvents.

The test also showed that rubbing the decal hard or numerous times greatly increased the damaging effect of a chemical or mixture. Thus, a better chemical or mixture had the right components to remove oily soil and rubber deposits chemically rather than with repeated hard rubbing.

In this testing, some of the chemicals and mixtures removed ink, but without damaging the appearance of the decal noticeably: the ink's glossy surface would be gone, but the chemical "self-cleaned" the damage it created. The chemical/mixture would first dissolve and smear ink across the decal. Then, with another swipe or two of the cleaning cloth, the chemical/mixture would pick up that smeared ink and remove it, leaving the decal with less gloss but no noticeable diminution of its visual impact.-

This first Example Eleven test was done with the following chemicals and mixtures of chemicals.

| CHEMICAL | To what extent did the chemical damage the decal inks? |
|---|---|
| 2024 Naphtha | Removed red and blue inks, but required some rubbing. Took gloss off cheapest decal. |
| Cypar-7 | Removed red and blue inks, but required some rubbing. Took gloss off cheapest decal. |
| DB | Inks came off readily |
| denatured ethanol | Took off inks easily. |
| EB | Inks came off readily |
| Ethanol | Took off some ink, but self-cleaned the decal. |
| Exxsol D115/145 | Took off blue ink. Took off very little red ink. |
| hexanol | Had the worst effect on decals of all these pure chemicals. |
| Isopar E | Took off extremely little blue ink. Took off no red ink. |
| isopropanol | Took off some ink, but self-cleaned the decal. |
| Mineral spirits | Did not damage the decal as readily as did the Cypar-7. |
| OS-10 siloxane | No effect. |
| Phillips Soltrol 10 hydrocarbon solvent | Removed very little blue ink or red ink. |
| PnB | About the same effect as Cypar-7. |
| PnP | Ink came off more easily than with the PnB. |
| Shell Sol 340 HT hydrocarbon solvent | Removed red and blue inks. Better than Cypar-7. |
| Soltrol 70 | More damaging than Isopar-E to blue ink. Less damaging than Isopar-E to red ink. |
| Solvo-Kleen | No effect. |
| Special Naphtholite | Took off blue ink. Took off very little red ink. |
| VM&P HT | Took off more blue ink than Isopar-E. Took off very little red ink. |

The next group of tests showed that, of the glycol ethers, PnB did the least amount of damage to decals. Also, the test indicated that a preferred glycol ether content is between 5% and 10% by volume.

| MIXTURE OF GLYCOL ETHER(S) AND DILUENT | To what extent did the mixture of chemicals damage the decal inks? |
|---|---|
| 3% PnB, 3% PnP, 94% Solvo-Kleen | Didn't remove gloss. A little ink came off but decals were fine. |
| 4% PnB, 2% PnP, 94% Solvo-Kleen | Very little blue ink came off. Extremely little red ink came off. |
| 5% DB, 95% water | No damage. |
| 5% EB, 95% water | No damage |
| 5% PnB, 5% PnP, 90% Solvo-Kleen | Removal of inks required lots of hard rubbing. |
| 5% PnB, 95% water | No damage. |
| 5% PnP, 95% water | No damage. |
| 6% PnB, 2% PnP, 92% Solvo-Kleen | Some blue ink came off, but not noticeably damaging to decal. |
| 6% PnB, 50% ethanol, 44% water | No damage to blue ink. A little red ink was damaged. |
| 10% PnB, 90% Solvo-Kleen | A little blue ink came off. Red ink came off. |
| 15% DB, 85% Solvo-Kleen | Ink came off, but less readily than with EB. |
| 15% EB, 85% Solvo-Kleen | Ink came off. |
| 15% PnB, 85% Solvo-Kleen | Ink came off, but less readily than with EB or DB. |
| 15% PnP, 85% Solvo-Kleen | Ink came off, but more readily than with PnB. |
| 25% DB, 75% Solvo-Kleen | Ink came off, but less readily than with EB. |
| 25% EB, 75% Solvo-Kleen | Ink came off. |
| 25% PnB, 75% Solvo-Kleen DB. | Ink came off, but less readily than with EB or |
| 25% PnP, 75% Solvo-Kleen | Ink came off, as readily as EB and DB. |
| 50% DB, 50% Solvo-Kleen | Ink came off almost as readily as with 100% DB. |
| 50% EB, 50% Solvo-Kleen | Ink came off almost as readily as with 100% EB. |
| 50% PnB, 50% Solvo-Kleen | Ink came off almost as readily as with 100% PnB. |
| 50% PnP, 50% Solvo-Kleen | Ink came off almost as readily as with 100% PnP. |

The following tests using the method of Example Eleven proved that ethanol is less damaging to decals than isopropanol. The tests also indicate that an upper limit of about 50% by volume of ethanol in the mixture is a preferred upper range for applications in which undue damage to decals is desirably avoided.

| MIXTURE OF ALCOHOL(S) AND DILUENT | To what extent did the mixture of chemicals damage the decal inks? |
|---|---|
| 20% isopropanol, 25% ethanol, 55% water | No damage, even with harder rubbing. |
| 25% isopropanol, 25% ethanol, 50% water | No damage. |
| 30% isopropanol, 30% ethanol, 40% water | No blue ink came off, Very little red came off. |
| 37.5% isopropanol, 37.5% ethanol, 25% water | Inks came off easily, but not as easily as with 75% isopropanol. |
| 40% isopropanol, 60% water | No damage. |
| 45% isopropanol, 55% water | No damage. |
| 50% ethanol, 50% water | No damage. |
| 50% isopropanol, 50% water | No damage. |
| 65% ethanol, 35% water | Ink came off, but less readily than with 90% ethanol mixture. |
| 75% ethanol, 25% water | Inks came off easily, but not as easily as with isopropanol. |
| 75% isopropanol, 25% water | Inks came off easily. |
| 90% ethanol, 10% water | Ink came off easily. |

The test below showed that individual chemicals which did no damage to any decals, even those of poor chemical resistance, were, when combined, able to damage decals. Thus, the combination of chemicals was more damaging than the individual chemical components.

| MIXTURE OF HYDROCARBON SOLVENT AND ALCOHOL | To what extent did the mixture of chemicals damage the decal inks? |
|---|---|
| 50% Isopar-E, 50% ethanol | Inks came off easily. |
| 50% VM&P HT, 50% ethanol | Inks came off easily. |

The following tests showed that the presence of an anti-static agent and siloxane did not protect decals and that certain hydrocarbon solvents were less damaging to decals, although not to a significant extent:

| MIXTURE OF GLYCOL ETHER, HYDROCARBON SOLVENT, ALCOHOL, AND MISCELLANEOUS CHEMICALS | To what extent did the mixture of chemicals damage the decal inks? |
|---|---|
| 3% PnB, 3% PnP, 44% VM&P HT, 50% ethanol | Inks came off easily. |
| 4% PnB, 2% PnP, 54% Isopar E, 40% ethanol | Inks came off easily. |
| 5% PnB, 5% PnP, 5% Cypar-7, 85% isopropanol | Removed blue ink noticeably. |
| 5% PnB, 5% PnP, 5% mineral spirits, 85% isopropanol | Removed blue ink noticeably. |
| 5% PnB, 5% PnP, 25% Cypar-7, 2.5% anti-static, 62.5% isopropanol | Removed blue ink noticeably. |
| 5% PnB, 5% PnP, 25% Cypar-7, 10% OS-10 siloxane, 55% isopropanol | Removed blue ink noticeably. |
| 5% PnB, 5% PnP, 25% Cypar-7, 65% isopropanol | Removed blue ink noticeably. |
| 5% PnB, 5% PnP, 25% Isopar E, 32.5% ethanol, 32.5% isopropanol | Removed inks easily. |
| 5% PnB, 5% PnP, 25% Isopar E, 65% isopropanol | Removed too much ink. |

-continued

| MIXTURE OF GLYCOL ETHER, HYDROCARBON SOLVENT, ALCOHOL, AND MISCELLANEOUS CHEMICALS | To what extent did the mixture of chemicals damage the decal inks? |
|---|---|
| 5% PnB, 5% PnP, 25% mineral spirits, 65% isopropanol | Removed blue ink noticeably. |
| 5% PnB, 5% PnP, 40% Exxsol D115/145, 25% ethanol, 25% isopropanol | Inks came off more easily than with VM&P HT. |
| 5% PnB, 5% PnP, 40% Isopar E, 25% ethanol, 25% isopropanol | Inks came off more easily than with VM&P HT or Exxsol D115/145. |
| 5% PnB, 5% PnP, 40% VM&P HT, 25% ethanol, 25% isopropanol | Inks came off easily, but not as easily as with Exxsol D115/145 or Isopar-E. |
| 5% PnB, 5% PnP, 40% VM&P HT, 50% ethanol | Inks came off easily. |
| 10% PnB, 24% Special Naphtholite, 40% ethanol, 26% water | Removed blue ink and some red ink. Did not self-clean. |
| 10% PnB, 30% VM&P HT, 60% ethanol | Removed inks easier than with 40% or 50% ethanol mixtures. |
| 10% PnB, 40% VM&P HT, 50% ethanol | Removed blue and red inks. |
| 10% PnB, 50% VM&P HT, 40% ethanol | Removed blue and red inks. |
| 10% PnB, 60% VM&P HT, 30% ethanol | Removed inks easier than with 40% or 50% ethanol mixtures. |

EXAMPLE TWELVE

The test of Example Eleven was done using Rain-X, SD-20, and WD-40 as cleaning agents. This test was done to check whether these cleaning agents which are used by a few racing professionals damaged decals. The Rain-X did a moderate amount of damage to decals. The SD-20 did no damage to decals. The WD-40 did no damage to decals.

EXAMPLE THIRTEEN

This test involved applying one of five chemicals to the types of vinyl used as backings for decals. Any resulting damage was recorded. This test revealed that none of these chemicals damaged the vinyl backings. The five chemicals were PnB, PnP, Special Naphtholite, ethanol, and isopropanol.

EXAMPLE FOURTEEN

Several pure chemicals and chemical mixtures were applied to the walls of a race track where a race vehicle had hit the wall during a race and left a smear of tire rubber on the wall. Two sets of tests were done: one with walls covered with white paint and one with walls covered with red paint.

This test revealed which of the following chemicals and mixtures of chemicals were best at removing rubber from race track walls.

The chemicals and mixtures tested were these:

| CHEMICAL OR MIXTURE | How did the chemical or mixture of chemicals affect the rubber smeared on a race track wall? |
|---|---|
| Cypar-7 | Removed thinner part of rubber smear very well; had to rub hard. |
| Ethanol | Removed rubber somewhat well. |
| Exxsol D115/145 | Removed rubber somewhat well. |
| Isopar E | Removed rubber somewhat well. |
| isopropanol | Removed rubber somewhat well. |
| Special Naphtholite | Removed rubber very well. |
| VM&P HT | Removed rubber very well. |
| 5% PnB, 5% PnP, 40% Exxsol D115/145, 50% isopropanol | Removed rubber well; did not have to rub too hard. |
| 5% PnB, 5% PnP, 40% Isopar E, 50% isopropanol | Removed rubber somewhat well. |
| 5% PnB, 5% PnP, 40% Special Naphtholite, 50% isopropanol | Removed rubber well; did not have to rub too hard. |
| 5% PnB, 5% PnP, 40% VM&P HT, 50% isopropanol | Removed rubber well; did not have to rub too hard; probably the best of the four mixtures. |

EXAMPLE FIFTEEN

A small amount of a mixture of 5% PnB, 5% PnP, 25% Cypar-7, and 65% isopropanol was poured onto a soiled race vehicle windshield, in particular, onto a spot on the windshield that had a rubber lump. A cloth was wiped over the spot to remove the rubber and other soil. They came off readily.

This test proved that the combination of a glycol ether, nonaromatic rubber solvent, and alcohol diluent did clean oily soil and tire rubber from a sensitive plastic surface.

EXAMPLE SIXTEEN

The following chemical and chemical mixtures were used to clean race vehicle windshields to determine if the chemicals and chemical mixtures could actually perform adequately in the demanding environment of an actual race. This test indicated which of these options were preferred by racing professionals.

| MIXTURE | Opinions of racing professionals |
|---|---|
| 2.5% PnB, 2.5% PnP, 25% Solvo-Kleen, 70% isopropanol | This mixture didn't clean fast enough. |
| 5% PnB, 5% PnP, 10% Cypar-7, 80% isopropanol | This mixture damaged decals. |
| 5% PnB, 5% PnP, 25% 2024 Naphtha, 65% isopropanol | This mixture left a little residue. It damaged decals. |
| 5% PnB, 5% PnP, 25% Cypar-7, 65% isopropanol | This mixture didn't evaporate fast enough. It left a little residue. It damaged decals. |
| 5% PnB, 5% PnP, 25% Solvo-Kleen, 65% isopropanol | This mixture didn't evaporate fast enough. |
| 5% PnB, 5% PnP, 25% VM&P HT, 65% isopropanol | This mixture left a little residue. It damaged decals to a small extent. It is the best of the six mixtures tested. |
| Solvo-Kleen | This chemical was not bad. |

Other embodiments of this invention will be apparent to those skilled in the art upon consideration of this specification or from practice of the invention disclosed herein. Various omissions, modifications, and changes to the principles and embodiments described herein may be made by one skilled in the art without departing from the true scope and spirit of the invention which is indicated by the following claims.

What is claimed is:

1. A method of cleaning a material contaminated with a radioactive contaminant, comprising the step of contacting the material with a cleaning composition comprising:

(a) an oil solubilizing amount of a degreaser;

(b) a rubber solvent; and (c) a polar, organic diluent; wherein at least one of the degreaser, rubber solvent, and the polar, organic diluent has a flash point of at least 30° F., and wherein the cleaning composition comprises 3 to 15 parts by weight of the degreaser per 20 to 60 parts of the rubber solvent and 20 to 60 parts by weight of diluent per 20 to 60 parts by weight of the rubber solvent.

2. The method of claim 1, wherein the cleaning composition comprises 5 to 10 parts by weight of the degreaser per 35 to 50 parts of the rubber solvent and 35 to 50 parts by weight of diluent per 35 to 50 parts by weight of the rubber solvent.

3. The method of claim 1, wherein the degreaser comprises a glycol ether.

4. The method of claim 3 wherein each of the degreaser, rubber solvent, and the polar, organic diluent has a flash point of at least 30° F.

5. The method of claim 1, wherein the rubber solvent comprises an aliphatic hydrocarbon solvent.

6. The method of claim 5, wherein the hydrocarbon solvent comprises an aliphatic naphtha.

7. The method of claim 1, wherein the diluent comprises an alcohol having at least about 5 carbon atoms.

8. The method of claim 7, wherein the alcohol is selected from hexanol and iso-hexanol.

9. The method of claim 1, wherein the degreaser comprises glycol ether, the rubber solvent comprises an aliphatic naphtha, and the diluent comprises an alcohol.

10. The method of claim 3 wherein each of the degreaser, rubber solvent, and the polar, organic diluent has a flash point of at least 50° F.

11. The method of claim 3 wherein each of the degreaser, rubber solvent, and the polar, organic diluent has a flash point of at least 65° F.

12. The method of claim 1, further comprising the step of contacting the material with at least one additional fluid composition.

13. The method of claim 1, wherein said contact with the additional fluid composition occurs after contact with the cleaning composition.

14. A method of hand cleaning comprising the steps of: providing a hand cleaning composition, comprising:

(a) an oil solubilizing amount of a degreaser;

(b) a rubber solvent; and (c) a polar, organic diluent; wherein at least one of the degreaser, rubber solvent, and the polar, organic diluent has a flash point of at least 30° F. and wherein the cleaning composition comprises 3 to 15 parts by weight of the degreaser per 20 to 60 parts of the rubber solvent and 20 to 60 parts by weight of diluent per 20 to 60 parts by weight of the rubber solvent; and contacting a soiled hand with the hand cleaning composition in a manner to clean the soiled hand.

15. The method of claim 14, wherein the cleaning composition comprises 5 to 10 parts by weight of the degreaser per 35 to 50 parts of the rubber solvent and 35 to 50 parts by weight of diluent per 35 to 50 parts by weight of the rubber solvent.

16. The method of claim 14, wherein the degreaser comprises a glycol ether.

17. The method of claim 14 wherein each of the degreaser, rubber solvent, and the polar, organic diluent has a flash point of at least 30° F.

18. The method of claim 14, wherein the rubber solvent comprises an aliphatic hydrocarbon solvent.

19. The method of claim 14, wherein the rubber solvent comprises an aliphatic naphtha.

20. The method of claim 14, wherein the diluent comprises an alcohol having at least about 5 carbon atoms.

21. The method of claim 20, wherein the alcohol is selected from hexanol and iso-hexanol.

22. The method of claim 14, wherein the degreaser comprises glycol ether, the rubber solvent comprises an aliphatic naphtha, and the diluent comprises an alcohol.

23. The method of claim 14 wherein each of the degreaser, rubber solvent, and the polar, organic diluent has a flash point of at least 50° F.

24. The method of claim 14 wherein each of the degreaser, rubber solvent, and the polar, organic diluent has a flash point of at least 65° F.

* * * * *

UNITED STATES PATENT AND TRADEMARK OFFICE

CERTIFICATE OF CORRECTION

PATENT NO. : 7,211,551 B2
APPLICATION NO. : 10/690208
DATED : May 1, 2007
INVENTOR(S) : McDonald It is certified that error appears in the above-identified patent and that said Letters Patent is hereby corrected as shown below:

Title Page, Item (57), 11th line of the "ABSTRACT," "an" should be --a--.

<u>Column 5</u>
Line 1, "invention are also provide" should be --invention also provide--.

Line 46, "Glycols" should be --Glycol--.

Signed and Sealed this

Third Day of July, 2007

JON W. DUDAS
*Director of the United States Patent and Trademark Office*